(12) United States Patent
Dihora et al.

(10) Patent No.: US 10,292,915 B2
(45) Date of Patent: May 21, 2019

(54) ANTIPERSPIRANT COMPOSITIONS

(71) Applicant: The Procter & Gamble Company, Cincinnati, OH (US)

(72) Inventors: Jiten Odhavji Dihora, Liberty Township, OH (US); Timothy Roy Nijakowski, Mason, OH (US); Jonathan Robert Cetti, Mason, OH (US); Robert Stanley Bobnock, Menasha, WI (US)

(73) Assignee: The Procter & Gamble Company, Cincinnati, OH (US)

( * ) Notice: Subject to any disclaimer, the term of this patent is extended or adjusted under 35 U.S.C. 154(b) by 170 days.

(21) Appl. No.: 14/989,620

(22) Filed: Jan. 6, 2016

(65) Prior Publication Data

US 2017/0189290 A1     Jul. 6, 2017

(51) Int. Cl.
| | |
|---|---|
| *A61K 8/11* | (2006.01) |
| *A61K 8/28* | (2006.01) |
| *A61K 8/26* | (2006.01) |
| *A61K 8/44* | (2006.01) |
| *A61Q 15/00* | (2006.01) |
| *A61K 8/81* | (2006.01) |

(52) U.S. Cl.
CPC ................. *A61K 8/28* (2013.01); *A61K 8/11* (2013.01); *A61K 8/26* (2013.01); *A61K 8/44* (2013.01); *A61K 8/8152* (2013.01); *A61Q 15/00* (2013.01); *A61K 2800/30* (2013.01); *A61K 2800/31* (2013.01); *A61K 2800/412* (2013.01); *A61K 2800/56* (2013.01); *A61K 2800/592* (2013.01)

(58) Field of Classification Search
None
See application file for complete search history.

(56) References Cited

U.S. PATENT DOCUMENTS

| | | |
|---|---|---|
| 2,730,456 A | 1/1956 | Green et al. |
| 2,800,457 A | 7/1957 | Green et al. |
| 2,800,458 A | 7/1957 | Green |
| 4,049,792 A | 9/1977 | Elsnau |
| 4,145,184 A | 3/1979 | Brain et al. |
| 4,152,272 A | 5/1979 | Young |
| 4,209,417 A | 6/1980 | Whyte |
| 4,515,705 A | 5/1985 | Moeddel |
| 4,552,811 A | 11/1985 | Brown et al. |
| 5,429,816 A | 7/1995 | Hofrichter et al. |
| 5,578,563 A | 11/1996 | Trinh et al. |
| 5,840,287 A | 11/1998 | Gusky et al. |
| 6,391,288 B1 * | 5/2002 | Miyazawa et al. ............. 424/59 |
| 6,592,990 B2 | 7/2003 | Schwantes |
| 7,736,695 B2 | 6/2010 | Schwantes et al. |
| 2010/0104611 A1 * | 4/2010 | Chan ...................... A61K 8/11 |
| | | 424/401 |
| 2013/0302392 A1 | 11/2013 | Mistry et al. |
| 2014/0079748 A1 | 3/2014 | Cetti et al. |
| 2015/0374593 A1 | 12/2015 | Cetti et al. |

FOREIGN PATENT DOCUMENTS

| | | |
|---|---|---|
| BE | 825146 A1 | 8/1975 |
| GB | 1 347 950 A | 2/1974 |

OTHER PUBLICATIONS

PCT International Search Report dated Mar. 24, 2017 (13 pages).

* cited by examiner

*Primary Examiner* — Nannette Holloman
(74) *Attorney, Agent, or Firm* — Kathleen Y. Carter

(57) ABSTRACT

An anhydrous antiperspirant composition includes a) an antiperspirant active; b) a perfume; and c) a microcapsule comprising a shell and a core, wherein the shell comprises a polymerized acrylate amine; wherein the composition has less than about 100 ppm of a residual metal catalyst and/or metal ion.

20 Claims, No Drawings

ANTIPERSPIRANT COMPOSITIONS

FIELD OF THE INVENTION

This application is directed to antiperspirant compositions which comprise a microcapsule comprising a tertiary amine and a metal catalyst.

BACKGROUND OF THE INVENTION

Antiperspirant compositions have become a staple in the personal hygiene routine for many people. Antiperspirant compositions can provide benefits to consumers such as combating wetness, reducing malodor, and/or delighting the consumer with the scent of a perfume. There is, however, room for improvement with respect to the delivery of perfume from antiperspirant compositions.

SUMMARY OF THE INVENTION

An anhydrous antiperspirant composition includes a) an antiperspirant active; b) a perfume; and c) a microcapsule comprising a shell and a core, wherein the shell comprises a multifunctional acrylic cross-linker and a co-polymerized acrylate amine; wherein the composition has less than about 100 ppm of a residual metal catalyst and/or metal ion.

DETAILED DESCRIPTION OF THE INVENTION

I. Definitions

As used herein, the following terms shall have the meaning specified thereafter:

"Ambient" refers to surrounding conditions at about one atmosphere of pressure, about 50% relative humidity, and about 25° C.

"Anhydrous" refers to compositions and/or components which are substantially free of water or free of water.

"Free of" means that the stated ingredient has not been added to the antiperspirant composition. However, the stated ingredient can incidentally form as a byproduct or a reaction product of the other components of the antiperspirant composition.

"Metal ion" means bound metal ions not including those that come in with the antiperspirant active.

"Onset of crystallization" means the temperature at which a material crystallizes from a liquid solution. All melting points and onsets of crystallization referenced herein, unless otherwise specified, are measured by the well-known technique of Differential Scanning calorimetry (DSC). For evaluation, a Perkin-Elmer 7 Series Thermal Analysis System Model DSC7 manufactured by Perkin-Elmer, Norwalk, Conn. is used.

"Residual metal catalyst" refers to bound metal ions in the antiperspirant composition which originated from raw materials used to make the microcapsule shell.

"Soft solid" when used with respect to an antiperspirant composition refers to an antiperspirant composition with a penetration force value of 700 gram force or less and utilizes an implement (like a dome on a package) for application to the underarm.

"Solid" when used with respect to an antiperspirant composition refers to a composition with a penetration force value of 600 gram force or more where the composition itself acts as the applicator to the underarm.

"Substantially free of" refers to about 3% or less, about 2% or less, about 1.5% or less, about 1% or less, or about 0.1% or less of a stated ingredient by weight of the antiperspirant composition.

II. Use of Microcapsules in an Anhydrous Antiperspirant Composition

Initial manufacture of anhydrous antiperspirant compositions containing microcapsules failed odor stability assessments. When these microcapsules were aged in the antiperspirant composition, the aged composition gave an off odor. The "off odor" is a noticeable character shift in the smell of the product after aging and is often graded on a scale. Since such accelerated aging of products is often used as an indicator of acceptable shelf life of a product, the development of an off odor during such testing is concerning.

Research began to try and understand the source of the off odor as the anhydrous antiperspirant composition itself did not generate an off odor upon accelerated aging and neither did all chemical types of microcapsules. As such, initial work focused on understanding the shell architecture and methods of making the shells of the microcapsules where the issue was encountered. These included microcapsules with shell materials like melamine formaldehyde, polyurea, and some polymerized acrylate amines (see Table 1 below).

TABLE 1

| SAMPLE # | SHELL CHEMISTRY | RESULTS OF 8 week 40° Accelerated Aging |
|---|---|---|
| A | Melamine Formaldehyde | Off odor |
| B | Polyurea | Off odor |
| C | Polymerized acrylate amine 1 | No off odor |
| D | Polymerized acrylate amine 2 | Off odor |

Looking to these shell chemistries, it was noted that all of these have amines. Thus, it was believed that the amines were potentially contributing to the development of the off odor. However, there was one amine based microcapsule that did not have the off odor, Sample C. In fact, this particular capsule contained the same shell chemistry to that of Sample D, which did give an off odor. Thus, it appeared that having an amine, alone, was not necessarily enough to generate the off odor. As such, the differences between the capsules in samples C and D was investigated.

Upon further analysis, capsules generating off odor with accelerated aging (sample D) were found to have high levels of bound metal ion impurities coming from at least some of the raw materials used to make the shell. Without being limited by theory, it is believed that these residual metal catalysts and/or metal ions are contributing to the degradation of the product under accelerated aging and thus the off odor generation over time.

One potential solution to the off odor generation caused by the residual metal catalysts/metal ions would be to include a chelant. This, however, is not a viable option in antiperspirant compositions as antiperspirant actives often contain metals and could be comprised by the addition of a chelant to the formula. Thus, polymerized acrylate amine containing microcapsules with little to no residual metal catalysts (100 ppm or less, by weight of the composition) have better stability in antiperspirant compositions than those with large amounts of residual metal catalysts (200 ppm or more, by weight of the composition).

Antiperspirant Compositions

Antiperspirant compositions comprise an antiperspirant active, a perfume, a carrier, and a microcapsule. The composition comprises less than about 100 ppm, about 90 ppm, more about 80 ppm, about 70 ppm, about 60 ppm, about 50 pm, about 40 ppm, about 30 ppm, about 20 ppm, about 10 ppm, or about 5 ppm, or the composition comprises zero ppm, of a metal catalyst and/or metal ion.

Antiperspirant compositions can be, for example, a soft solid antiperspirant, a solid antiperspirant, or an aerosol antiperspirant. The antiperspirant composition can be anhydrous.

Antiperspirant Active

Antiperspirant compositions can include an antiperspirant active suitable for application to human skin. The concentration of the antiperspirant active in the antiperspirant composition should be sufficient to provide the desired enhanced wetness protection. For example, the active can be present in an amount of from about 0.1%, about 0.5%, about 1%, or about 5%; to about 60%, about 35%, about 25% or about 20%, by weight of the antiperspirant composition. These weight percentages are calculated on an anhydrous metal salt basis exclusive of water and any complexing agents such as glycine, glycine salts, or other complexing agents.

An antiperspirant active can include any compound, composition, or other material having antiperspirant activity. Such actives can include astringent metallic salts, like inorganic and organic salts of aluminum, zirconium and zinc, as well as mixtures thereof. For example, the antiperspirant active can include zirconium-containing salts or materials, such as zirconyl oxyhalides, zirconyl hydroxyhalides, and mixtures thereof; and/or aluminum-containing salts such as, for example, aluminum halides, aluminum chlorohydrate, aluminum hydroxyhalides, and mixtures thereof.

1. Aluminum Salts

Aluminum salts useful herein can include those that conform to the formula:

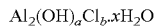

$Al_2(OH)_aCl_b \cdot xH_2O$ wherein a is from about 2 to about 5; the sum of a and b is about 6; x is from about 1 to about 6; where a, b, and x can have non-integer values. For example, aluminum chlorohydroxides referred to as "5/6 basic chlorohydroxide," wherein a is about 5 and "2/3 basic chlorohydroxide", wherein a=4 can be used.

A general description of these aluminum salts can be found in *Antiperspirants and Deodorants*, Cosmetic Science and Technology Series Vol. 20, $2^{nd}$ edition, edited by Karl Laden. Mixtures of aluminum salts are described in British Patent Specification 1,347,950, filed in the name of Shin et al. and published Feb. 24, 1974.

2. Zirconium Salts

Zirconium salts useful herein can include those which conform to the formula:

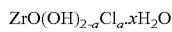

$ZrO(OH)_{2-a}Cl_a \cdot xH_2O$ wherein a is from about 1.5 to about 1.87; x is from about 1 to about 7; and wherein a and x can both have non-integer values. These zirconium salts are described in Belgian Patent 825,146, issued to Schmitz on Aug. 4, 1975. Useful to the present invention are zirconium salt complexes that additionally contain aluminum and glycine, commonly known as "ZAG complexes". These complexes can contain aluminum chlorohydroxide and zirconyl hydroxy chloride conforming to the above-described formulas. Examples of two such complexes include aluminum zirconium trichlorohydrex and aluminum zirconium tetrachlorohydrex.

The antiperspirant active can comprise, for example, aluminum zirconium tetrachlorohydrex gly; aluminum zirconium tetrachlorohydrate, aluminum zirconium pentachlorohydrate, aluminum zirconium pentachlorohydrex gly, aluminum zirconium trichlorohydrex gly, aluminum zirconium trichlorohydrate, aluminum zirconium octachlorohydrate, aluminum zirconium octachlorohydrex glycine, aluminum chlorohydrate, aluminum chlorohydrex polyethylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol or a combination thereof.

Carrier

Antiperspirant compositions can also include a carrier. The carrier can be present, for example, at concentrations ranging from about 10%, about 15%, about 20%, about 25%; to about 99%, about 70%, about 60%, or about 50%, by weight of the antiperspirant composition. Such concentrations will vary depending upon variables such as product form, desired product hardness, and selection of other ingredients in the antiperspirant composition. The carrier can be any anhydrous carrier known for use in antiperspirant compositions or otherwise suitable for topical application to the skin. For example, anhydrous carriers can include, but are not limited to, volatile and nonvolatile fluids.

A. Volatile Fluid

The antiperspirant compositions can also include a volatile fluid such as a volatile silicone carrier. Volatile fluids are present, for example, at concentrations ranging from about 20% or from about 30%; to about 80%, or no about 60%, by weight of the antiperspirant composition. The volatile silicone of the solvent can be cyclic, linear, and/or branched chain silicone. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976).

The volatile silicone can be a cyclic silicone. The cyclic silicone can have from about 3 silicone atoms, or from about 5 silicone atoms; to about 7 silicone atoms, or to about 6 silicone atoms. For example, volatile silicones can be used which conform to the formula:

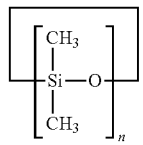

wherein n is from about 3, or from about 5; to about 7, or to about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

B. Non-Volatile Fluid

A non-volatile fluid can also be present, for example, at concentrations ranging from about 1%, from about 2%; to about 20%, or about 15%, by weight of the antiperspirant composition.

1. Non-Volatile Organic Fluids

The non-volatile organic fluid can be present at concentrations ranging from about 1%, from about 2% but no more than about 20% or no more than about 15%, by weight of the antiperspirant composition.

Non-limiting examples of nonvolatile organic fluids include, but are not limited to, mineral oil, PPG-14 butyl ether, isopropyl myristate, petrolatum, butyl stearate, cetyl octanoate, butyl myristate, myristyl myristate, C12-15 alkylbenzoate (e.g., Finsolv™), dipropylene glycol dibenzoate, PPG-15 stearyl ether benzoate and blends thereof (e.g. Finsolv TPP), neopentyl glycol diheptanoate (e.g. Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanate, hydrogenated polyisobutane, and isobutyl stearate. Many such other carrier liquids are disclosed in U.S. Pat. No. 6,013,248 (Luebbe et al.) and U.S. Pat. No. 5,968,489 (Swaile et al.).

2. Nonvolatile Silicone Fluids

The antiperspirant composition can also include a nonvolatile silicone fluid. The non-volatile silicone fluid can be a liquid at or below human skin temperature, or otherwise in liquid form within a antiperspirant composition, like an anhydrous antiperspirant composition, during or shortly after topical application. The concentration of the nonvolatile silicone can be from about 1%, from about 2%; to about 15%, about 10%, by weight of the antiperspirant composition. Nonvolatile silicone fluids can include those which conform to the formula:

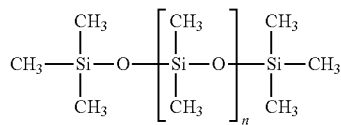

wherein n is greater than or equal to 1. These linear silicone materials can generally have viscosity values of from about 5 centistokes, from about 10 centistokes; to about 100,000 centistokes, about 500 centistokes, about 200 centistokes, or about 50 centistokes, as measured under ambient conditions.

Specific non limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF18(350) Silicone Fluids (available from G.E. Silicones).

Low surface tension non-volatile solvent can be also be used. Such solvents can be selected from the group consisting of dimethicones, dimethicone copolyols, phenyl trimethicones, alkyl dimethicones, alkyl methicones, and mixtures thereof. Low surface tension non-volatile solvents are also described in U.S. Pat. No. 6,835,373 (Kolodzik et al.).

Microcapsules

The antiperspirant compositions herein can include microcapsules. The microcapsules can have a shell and a core. The core may include a benefit agent which is encapsulated by the shell. The shells of the microcapsules can be made from synthetic polymeric materials or naturally-occurring polymers. The shell material comprises a cross-linked polyacrylate containing amine functionalities.

The microcapsule's shell can comprise a reaction product of a first mixture in the presence of a second mixture comprising an emulsifier, the first mixture comprising a reaction product of i) an oil soluble or dispersible aminoacrylate with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. In some examples, said amine is an aminoalkyl acrylate or aminoalkyl methacrylate.

The microcapsules can have shells with amine functionality made from any material in any size, shape, and configuration known in the art. Some or all of the shells can include a polyacrylate material, such as a polyacrylate random copolymer. For example, the polyacrylate random copolymer can have a total polyacrylate mass, which includes ingredients selected from the group including: amine content of 0.2-2.0% of total polyacrylate mass; carboxylic acid of 0.6-6.0% of total polyacrylate mass; and a combination of amine content of 0.1-1.0% and carboxylic acid of 0.3-3.0% of total polyacrylate mass.

The microcapsules can include a core material and a shell surrounding the core material, wherein the shell comprises: a plurality of amine monomers selected from the group consisting of aminoalkyl acrylates, alkyl aminoalkyl acrylates, dialkyl aminoalykl acrylates, aminoalkyl methacrylates, alkylamino aminoalkyl methacrylates, dialkyl aminoalykl methacrylates, tertiarybutyl aminoethyl methacrylates, diethylaminoethyl methacrylates, dimethylaminoethyl methacrylates, dipropylaminoethyl methacrylates, and mixtures thereof; and a plurality of multifunctional monomers or multifunctional oligomers.

Non-limiting examples of microcapsules include microcapsules that comprise a shell comprising an amine selected from the group consisting of diethylaminoethyl methacrylate, dimethylaminoethyl methacrylate, tertiarybutyl aminoethyl methacrylate; and combinations thereof; a core material encapsulated by said shell, said core material comprising about 10% to about 60% of a material selected from the group consisting of mono, di- and tri-esters of $C_4$-$C_{24}$ fatty acids and glycerin; isopropyl myristate, soybean oil, hexadecanoic acid, methyl ester, isododecane, and combinations thereof, by weight of the microcapsule; and about 10% to about 90% of a perfume material, by weight of the microcapsule; wherein said microcapsules have a volume weighted fracture strength from 0.1 MPa to 25 MPa, preferably from 0.8 MPa to 20 MPa, more preferably from 1.0 MPa to 15 MPa; wherein said microcapsules have a median volume-weighted particle size from 10 microns to 30 microns. When a microcapsule's shell includes a polyacrylate material, the polyacrylate material can form 5-100% of the overall mass, or any integer value for percentage in this range, or any range formed by any of these values for percentage, of the shell. As examples, the polyacrylate material can form at least 5%, at least 10%, at least 25%, at least 33%, at least 50%, at least 70%, or at least 90% of the overall mass of the shell.

The microcapsules can be friable microcapsules. A friable microcapsule is configured to release its core material when its shell is ruptured. The rupture can be caused by forces applied to the shell during mechanical interactions. The microcapsules can have a median volume weighted fracture strength of from about 0.1 MPa to about 25.0 MPa, when measured according to the Fracture Strength Test Method, or any incremental value expressed in 0.1 mega Pascals in this range, or any range formed by any of these values for fracture strength. As an example, the microcapsules can have a median volume weighted fracture strength of 0.5-25.0 mega Pascals (MPa), alternatively from 0.5-20.0 mega Pascals (MPa), 0.5-15.0 mega Pascals (MPa), or alternatively from 0.5-10.0 mega Pascals (MPa).

The microcapsules can have a median volume-weighted particle size of from 2 microns to 80 microns, from 10 microns to 30 microns, or from 10 microns to 20 microns, as determined by the Test Method for Determining Median Volume-Weighted Particle Size of Microcapsules described herein.

The microcapsules can have various core material to shell weight ratios. The microcapsules can have a core material to shell ratio that is greater than or equal to: 10% to 90%, 30% to 70%, 50% to 50%, 60% to 40%, 70% to 30%, 75% to 25%, 80% to 20%, 85% to 15%, 90% to 10%, and 95% to 5%.

The microcapsules can have various shell thicknesses. The microcapsules can have a shell with an overall thickness of 1-2000 nanometers, or any integer value for nanometers in this range, or any range formed by any of these values for thickness. As a non-limiting example, the microcapsules can have a shell with an overall thickness of 2-1100 nanometers.

The microcapsules can also encapsulate one or more benefit agents. The benefit agent(s) include, but are not limited to, one or more of chromogens, dyes, cooling sensates, warming sensates, perfumes, oils, pigments, in any combination. When the benefit agent includes a perfume, said perfume can comprise from about 2% to about 80%, from about 20% to about 70%, from about 30% to about 60% of a perfume raw material with a C log P greater than −0.5, or even from about 0.5 to about 4.5. For example, the perfume encapsulated can have a C log P of less than 4.5, less than 4, or less than 3. The microcapsule can be anionic, cationic, zwitterionic, or have a neutral charge. The benefit agents can be in the form of solids and/or liquids.

The microcapsules can encapsulate an oil soluble material in addition to the benefit agent. Non-limiting examples of the oil soluble material include mono, di- and tri-esters of $C_4$-$C_{24}$ fatty acids and glycerin; butyl oleate; hydrogenated castor oil; castor oil; mineral oil; capryllic triglyceride; vegetable oil; geranyl palmitate; silicone oil; isopropyl myristate, soybean oil, hexadecanoic acid, methyl ester, isododecane, and combinations thereof, in addition to the encapsulated benefit agent. The oil soluble material can have a C log P of about 4 or greater, at least 4.5 or greater, at least 5 or greater, at least 7 or greater, or at least 11 or greater.

Processes for making microcapsules are well known. Various processes for microencapsulation, and exemplary methods and materials, are set forth in U.S. Pat. Nos. 6,592,990; 2,730,456; 2,800,457; 2,800,458; 4,552,811; and U.S. 2006/0263518 A1.

The microcapsule can be dried, for example, spray-dried to form dried microcapsules. Dried microcapsules can be in the form of a powder and have a water content of 15% or less, 10% or less, 5% or less, or 1% or less, by weight of the powder.

Perfumes

The antiperspirant compositions can include one or more perfumes. As used herein, "perfume" is used to indicate any odoriferous material. Any perfume that is cosmetically acceptable can be used in the antiperspirant composition. For example, the perfume can be one that is a liquid at room temperature. Generally, the perfume(s) can be present at a level from about 0.01% to about 20%, from about 0.1% to about 10%, from about 0.25% to about 5%, or from about 0.5% to about 3%, by weight of the antiperspirant composition.

The antiperspirant compositions can include a parent perfume and one or more encapsulated perfumes that may differ or be the same as the parent perfume. For example, the composition can include a parent perfume and a non-parent perfume. A parent perfume refers to a perfume that is dispersed throughout the composition and is typically not encapsulated when added to the composition. Herein, a non-parent perfume refers to a perfume that is encapsulated with an encapsulating material prior to inclusion into a composition and optionally may differ from a parent perfume. Non-limiting examples of differences between a perfume and a non-parent perfume include differences in chemical make-up.

A wide variety of chemicals are known as perfumes, including aldehydes, ketones, and esters. More commonly, naturally occurring plant and animal oils and exudates comprising complex mixtures of various chemical components are known for use as perfumes. Non-limiting examples of the perfumes useful herein include pro-perfumes such as acetal pro-perfumes, ketal pro-perfumes, ester pro-perfumes, hydrolyzable inorganic-organic pro-perfumes, and mixtures thereof. The perfumes can be released from the pro-perfumes in a number of ways. For example, the perfume can be released as a result of simple hydrolysis, or by a shift in an equilibrium reaction, or by a pH-change, or by enzymatic release. The perfumes herein can be relatively simple in their chemical make-up, comprising a single chemical, or can comprise highly sophisticated complex mixtures of natural and synthetic chemical components, all chosen to provide any desired odor.

The perfumes can have a boiling point (BP) of about 500° C. or lower, about 400° C. or lower, or about 350° C. or lower. The BP of many perfumes are disclosed in *Perfume and Flavor Chemicals* (Aroma Chemicals), Steffen Arctander (1969). The C log P value of the perfumes can be about 0.1 or greater, about 0.5 or greater, about 1.0 or greater, and about 1.2 or greater. As used herein, "C log P" means the logarithm to the base 10 of the octanol/water partition coefficient. The C log P can be readily calculated from a program called "CLOGP" which is available from Daylight Chemical Information Systems Inc., Irvine Calif., USA. Octanol/water partition coefficients are described in more detail in U.S. Pat. No. 5,578,563.

Suitable perfumes are also disclosed in U.S. Pat. Nos. 4,145,184, 4,209,417, 4,515,705, and 4,152,272. Non-limiting examples of perfumes include animal perfumes such as musk oil, civet, castoreum, ambergris, plant perfumes such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomile oil, clove oil, sage oil, neroli oil, labdanum oil, *eucalyptus* oil, *verbena* oil, *mimosa* extract, *narcissus* extract, carrot seed extract, jasmine extract, olibanum extract, rose extract, and mixtures thereof.

Other examples of suitable perfumes include, but are not limited to, chemical substances such as acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, cis-3-hexenyl methyl carbonate, citral, citronellol and ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltolide, fenchone, fruity esters such as ethyl 2-methyl butyrate, galaxolide, geraniol and ester derivatives, helional, 2-heptonone, hexenol, α-hexylcinnamic aldehyde, hydroxycitrolnellal, indole, isoamyl acetate, isoeugenol acetate, ionones, isoeugenol, isoamyl iso-valerate, iso E super, limonene, linalool, lilial, linalyl acetate, lyral, majantol, canol, melonal, menthol, p-methylacetophenone, methyl anthranilate, methyl cedrylone, methyl dihydrojasmonate, methyl eugenol, methyl ionone, methyl-α-naphthyl ketone, methylphenylcarbinyl acetate, mugetanol, γ-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohexanol, γ-undecalactone, undecenal, vanillin, veloutone, verdox, and mixtures thereof.

Structurants

Antiperspirant compositions can also include a structurant to help provide the antiperspirant composition with the desired viscosity, rheology, texture and/or product hardness, or to otherwise help suspend any dispersed solids or liquids within the antiperspirant composition. The term "structurant" can include any material known or otherwise effective in providing suspending, gelling, viscosifying, solidifying, or thickening properties to the antiperspirant composition or which otherwise provide structure to the final product form. Non-limiting examples of structurants include, for example, gelling agents, polymeric or nonpolymeric agents, inorganic thickening agents, or viscosifying agents. Non-limiting examples of thickening agents include, for example, organic solids, silicone solids, crystalline or other gellants, inorganic particulates such as clays or silicas, or combinations thereof.

The concentration and type of the structurant selected for use in the antiperspirant composition can vary depending upon the desired product form, viscosity, and hardness. The thickening agents suitable for use herein, can have a concentration range from about 0.1%, about 3%, or about 5%; to about 35%, about 20%, or about 10%, by weight of the antiperspirant composition. Soft solids will often contain a lower amount of structurant than solid compositions. For example, a soft solid can contain from about 1.0% to about 9%, by weight of the composition, while a solid composition can contain from about 15% to about 25%, by weight of the antiperspirant composition, of a structurant. This is not a hard and fast rule, however, as a soft solid product with a higher structurant value can be formed by, for example, shearing the product as it is dispensed from a package.

Non-limiting examples of suitable gelling agents include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof. Optionally, the microcapsules can be premixed with such gellants prior to incorporation into the antiperspirant composition.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

Other suitable gelling agents include amide gellants such as di-substituted or branched monoamide gellants, monosubstituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

Still other examples of suitable gelling agents include fatty alcohols having at least about 8 carbon atoms, at least about 12 carbon atoms but no more than about 40 carbon atoms, no more than about 30 carbon atoms, or no more than about 18 carbon atoms. For example, fatty alcohols include but are not limited to cetyl alcohol, myristyl alcohol, stearyl alcohol and combinations thereof.

Non-limiting examples of suitable triglyceride gellants include tristearin, hydrogenated vegetable oil, trihydroxysterin (Thixcin® R, available from Rheox, Inc.), rape seed oil, castor wax, fish oils, tripalmitin, Syncrowax® HRC and Syncrowax® HGL-C(Syncrowax® available from Croda, Inc.).

Other suitable thickening agents include waxes or wax-like materials having a melt point of above 65° C., more typically from about 65° C. to about 130° C., examples of which include, but are not limited to, waxes such as beeswax, carnauba, bayberry, candelilla, montan, ozokerite, ceresin, hydrogenated castor oil (castor wax), synthetic waxes and microcrystalline waxes. The synthetic wax can be, for example, but not limited to, a polyethylene, a polymethylene, or a combination thereof. Some suitable polymethylenes can have a melting point from about 65° C. to about 75° C. Examples of some suitable polyethylenes include those with a melting point from about 60° C. to about 95° C. Other high melting point waxes are described in U.S. Pat. No. 4,049,792, Elsnau, issued Sep. 20, 1977.

Further structurants for use in the antiperspirant compositions can include inorganic particulate thickening agents such as clays and colloidal pyrogenic silica pigments. For example, but not limited to, colloidal pyrogenic silica pigments such as Cab-O-Sil®, a submicroscopic particulated pyrogenic silica can be used. Other known or otherwise effective inorganic particulate thickening agents that are commonly used in the art can also be used in the antiperspirant compositions described herein. Concentrations of particulate thickening agents can range, for example, from about 0.1%, about 1%, or about 5%; to about 35%, about 15%, about 10% or about 8%, by weight of the antiperspirant composition.

Clay structurants include montmorillonite clays, non-limiting examples of which include bentonites, hectorites, and colloidal magnesium aluminum silicates. These and other clays can be hydrophobically treated, and when treated will generally be used in combination with a clay activator. Non-limiting examples of suitable clay activators include propylene carbonate, ethanol, and combinations thereof. When clay activators are present, the amount of clay activator can be in a range of from about 40%, about 25%, or about 15%; to about 75%, about 60%, or about 50%, by weight of the clay.

Surfactant

The antiperspirant compositions can include a surfactant. A surfactant is generally present at a level of about 0.05% to about 5%, by weight of the antiperspirant composition, but can contain, from about 0.5% to about 5.0%; from about 1.0% to about 4%; from about 1.5% to about 3.5%; from about 1.75% to about 2.5%; about 2%, or any combination thereof. The surfactant can have a HLB range of about 2 to about 14; about 6 to about 12; about 8 to about 10; or any combination thereof. The surfactant can be free of polyoxyethylene sorbitan fatty acids. The surfactant can comprise, for example, a $C_{20-40}$ Pareth-10. Another suitable surfactant is a nonionic exthoxylated linear alcohol with a carbon chain length of 20-40. Suitable surfactants include PERFORMATHOX™ 450 ethoxylate.

Propellant

The antiperspirant composition can be in the form of an aerosol. Thus, the composition can include a propellant and be stored in a spray device. The spray device can comprise a propellant stored in one or more reservoirs of the container. The propellant may be stored in the same reservoir as an antiperspirant composition or a separate reservoir, although it is preferred that the propellant is stored within the same reservoir as the antiperspirant composition. The propellant may be present in a liquefied form that is miscible with liquid carriers of the antiperspirant composition as well as gaseous state within a head space of the reservoir. The liquid propellant and the antiperspirant composition form a mixture that travels through the container, eventually exiting the container where the liquid propellant vaporizes to from a spray. The propellant may have a concentration from about 25% to about 90%, or from about 40% to about 85%, or from about 50% to about 80%, by weight of the antiperspirant composition.

A wide variety of propellants may be used with the spray devices and antiperspirant compositions described herein, although in some embodiments the spray device is substantially free of compressed gas propellants such as nitrogen, air and carbon dioxide. Some suitable propellants may have a boiling point (at atmospheric pressure) within the range of from about −45° C. to about 5° C. Some suitable propellants may include chemically-inert hydrocarbons such as propane, n-butane, isobutane and cyclopropane, and mixtures thereof, as well as halogenated hydrocarbons such as dichlorodifluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), dimethyl ether and monochlorodifluoromethane, and mixtures thereof. Some propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), HFO1234 (trans-1,3,3,3-tetrafluoropropene) and 152A (1,1 difluoroethane).

Other Materials

The antiperspirant compositions can also include other materials known for use in antiperspirant, deodorant or other personal care products, including those materials that are known to be suitable for topical application to skin. Non-limiting examples include dyes or colorants, emulsifiers, distributing agents, pharmaceuticals or other topical actives, skin conditioning agents or actives, deodorant agents, antimicrobials, preservatives, surfactants, processing aides such as viscosity modifiers and wash-off aids.

Other Perfume Delivery Systems

The composition can also contain one or more other delivery systems for providing one or more benefit agents, in addition or in place of the microcapsules. The additional delivery system(s) can differ in kind from the microcapsules. For example, wherein the microcapsule are friable and encapsulate a perfume, the additional delivery system can be an additional perfume delivery system, such as a moisture-triggered perfume delivery system. Non-limiting examples of moisture-triggered perfume delivery systems include cyclic oligosaccharide, starch (or other polysaccharide material), or combinations thereof.

Starch

Examples of starches suitable for use can be made from raw starch, pregelatinized starch, modified starch derived from tubers, legumes, cereal and grains for example corn starch, wheat starch, rice starch, waxy corn starch, oat starch, cassava starch, waxy barley starch, waxy rice starch, sweet rice starch, amioca, potato starch, tapioca starch, and mixtures thereof. Further examples of modified starches can include hydrolyzed starch, acid thinned starch, starch having hydrophobic groups, such as starch esters of long chain hydrocarbons (C5 or greater), starch acetates, starch octenyl succinate, and mixtures thereof. An example of starch esters includes starch octenyl succinates.

Starch esters will typically have a degree of substitution in the range of from 0.01% to 10%. The hydrocarbon part of the modifying ester can be a C 5 to a C 16 carbon chain. As stated above, one example of a starch ester is octenyl succinate. The octenyl succinate (OSAN) can be a substituted waxy corn starch of various types such as 1) waxy starch, acid thinned and OSAN substituted, 2) blend of corn syrup solids: waxy starch, OSAN substituted and dextrinized, 3) waxy starch: OSAN substituted and dextrinised, 4) blend of corn syrup solids or maltodextrins with waxy starch: acid thinned OSAN substituted then cooked and spray dried, 5) waxy starch: acid thinned OSAN substituted then cooked and spray dried; and 6) the high and low viscosities of the above modifications (based on the level of acid treatment) can also be used. Mixtures of these, particularly mixtures of the high and low viscosity modified starches, are also suitable.

The term "hydrolyzed starch" refers to oligosaccharide-type materials that are typically obtained by acid and/or enzymatic hydrolysis of starches, like corn starch. A starch ester can be included in the starch water-mixture. The hydrolyzed starches, particularly for starch esters or mixture of starch esters, can have Dextrose Equivalent (DE) values of from 20 to 80, from 20 to 50, or even 25 to 38 DE. The DE value is a measure of the reducing equivalence of the hydrolyzed starch referenced to dextrose and expressed as a percent (on a dry basis). The higher the DE value, the more reducing sugars present. A method for determining DE values can be found in Standard Analytical Methods of the Member Companies of Corn Industries Research Foundation, 6th ed. Corn Refineries Association, Inc. Washington, D.C. 1980, D-52.

One example of a modified starch comprises a starch derivative containing a hydrophobic group, or both a hydrophobic and a hydrophilic group, which has been degraded by at least one enzyme capable of cleaving the 1, 4 linkages of the starch molecule from the non-reducing ends to produce short chained saccharides to provide high oxidation resistance while maintaining substantially high molecular weight portions of the starch base. Such starches are described in EP-A-922 449.

Starches can also comprise monosaccharides such as glucose, disaccharides, trisaccharides, oligosaccharides, polysaccharides, and linear sugar alcohols such as mannite. As for the polysaccharides, mention can be made of starch, cellulose, chitin, chitosan, hemicellulose, pectin, pullulan, agar, alginic acid, carageenan, dextrin, trehalose, and the like.

Cyclic Oligosaccharide

As used herein, the term "cyclic oligosaccharide" means a cyclic structure comprising six or more saccharide units. The cyclic oligosaccharides can have six, seven, or eight saccharide units or mixtures thereof. It is common in the art to refer to six, seven and eight membered cyclic oligosaccharides as α, β, and γ, respectively. The cyclic oligosaccharides that can be useful include those that are soluble in water, ethanol, or both water and ethanol. The cyclic oligosaccharides useful herein can have a solubility of at least about 0.1 g/100 ml, at 25° C. and 1 atm of pressure in either water, ethanol, or both water and ethanol. The antiperspirant compositions disclosed herein can comprise from about 0.001% to about 40%, from about OA % to about 25%, from about 0.3% to about 20%, from about 0.5% to about 10%, or from about 0.75% to about 5%, by weight of the antiperspirant composition, of a cyclic oligosaccharide. The antiperspirant compositions disclosed herein can comprise from 0.001% to 40%, from 0.1% to 25%, from 0.3% to 20%, from 0.5% to 10%, or from 0.75% to 5%, by weight of the antiperspirant composition, of a cyclic oligosaccharide.

The cyclic oligosaccharide can comprise any suitable saccharide or mixture of saccharides. Examples of suitable saccharides include, but are not limited to, glucose, fructose, mannose, galactose, maltose, and mixtures thereof. The cyclic oligosaccharide, or mixture of cyclic oligosaccharides, can be substituted by any suitable substituent or mixture of substituents. Herein, the use of the term "mixture of substituents" means that two or more different suitable substituents can be substituted onto one cyclic oligosaccharide. Suitable examples of substituents include, but are not limited to, alkyl groups, hydroxyalkyl groups, dihydroxyalkyl groups, carboxyalkyl groups, aryl groups, maltosyl groups, allyl groups, benzyl groups, alkanoyl groups, and mixtures thereof. These substituents can be saturated or unsaturated, straight or branched chain. For example, the substituents can include saturated and straight chain alkyl groups, hydroxyalkyl groups, and mixtures thereof. The alkyl and hydroxyalkyl substituents, for example, can also be selected from $C_1$-$C_8$ alkyl or hydroxyalkyl groups, alkyl and hydroxyalkyl substituents from $C_1$-$C_6$ alkyl or hydroxyalkyl groups, and alkyl and hydroxyalkyl substituents from $C_1$-$C_4$ alkyl or hydroxyalkyl groups. The alkyl and hydroxyalkyl substituents can be, for example, propyl, ethyl, methyl, and hydroxypropyl.

In addition to the substituents themselves, the cyclic oligosaccharides can have an average degree of substitution of at least 1.6, wherein the term "degree of substitution" means the average number of substituents per saccharide unit. For example, the cyclic oligosaccharides can have an average degree of substitution of less than about 2.8 or from about 1.7 to about 2.0. The average number of substituents can be determined using common Nuclear Magnetic Resonance techniques known in the art. Examples of cyclic oligosaccharides useful herein include cyclodextrins such as methyl-α-cyclodextrins, methyl-β-cyclodextrins, hydroxypropyl-α-cyclodextrins, hydroxypropyl-β-cyclodextrins, and mixtures thereof. The cyclodextrins can be inn the form of particles. The cyclodextrins can also be spray-dried and can also be spray-dried particles. The cyclodextrins can also be complexed with a perfume to form a complexed cyclodextrin.

EXAMPLES

Formulation examples A through D are prepared by conventional mixing techniques, adding all of the raw materials (except aluminum zirconium antiperspirant actives, perfume, and perfume technologies, (for example, beta-cyclodextrin perfume complex, perfume microcapsules, and starch encapsulated perfume)) to a mix tank, heating it to a temperature of 88° C. to melt the structurants and other higher melt point ingredients, and holding it at that temperature until the ingredients are melted. At this point, the batch is cooled to 70-75° C. and the aluminum zirconium antiperspirant actives, perfume and perfume technologies are added to the tank. The composition is mixed here for at least 15 minutes before it is cooled to 55-60° C. and poured into canisters.

| Common/Trade name | Solid Formula A | Solid Formula B | Solid Formula C | Solid Formula D |
|---|---|---|---|---|
| Cyclopentasiloxane | Q.S. | Q.S. | Q.S. | Q.S. |
| PPG-14 Butyl Ether | 7.00 | 6.5 | — | 5.00 |
| Phenyl Trimethicone | | 3 | — | — |
| Dimethicone 50 cst | 1.00 | — | 1.5 | 0.5 |
| Petrolatum | 3.00 | — | 2.5 | 2.0 |
| Mineral Oil | 5.00 | 5 | 3.00 | 8.0 |
| Stearyl Alcohol | 12.35 | 14.0 | 13.1 | 12.5 |
| Hydrogenated Castor Oil MP80 Deodorized | 2.75 | 3.85 | 2.5 | 3.0 |
| Behenyl Alcohol | 0.20 | 0.25 | 0.2 | 0.3 |
| Performathox 450 Ethoxylate | 2.00 | — | — | 1.0 |
| Talc | 1.50 | 3.0 | 2.0 | 0.5 |
| Aluminum Zirconium Tetrachlorohydrex Gly | 26.67 | | 26.00 | |
| Aluminum Zirconium Tricholorohydrex Gly | | 24.00 | | 22.5 |
| beta-cylcodextrin Perfume complex | 4.00 | 3.0 | — | 2.0 |
| Perfume Microcapsules | 2.5 | 1.5 | 2.0 | 2.0 |
| Starch Encapsulated Perfume | | | 1.5 | 2.0 |
| Parent Perfume | 1.0 | 2.5 | 1.5 | 0.75 |
| Total | 100.00 | 100.00 | 100.00 | 100.00 |

Examples/Combinations

A. An anhydrous antiperspirant composition, comprising: a) an antiperspirant active; b) a perfume; and c) a microcapsule comprising a shell and a core, wherein the shell comprises a polymerized acrylate amine; wherein the composition has less than 100 ppm, less than 90 ppm, less than 80 ppm, less than 70 ppm, less than 60 ppm, less than 50 pm, less than 40 ppm, less than 30 ppm, less than 20 ppm, less than 10 ppm, less than 5 ppm, or zero ppm, of a residual metal catalyst.

B. An anhydrous antiperspirant composition, comprising: a) an antiperspirant active; b) a perfume; and c) a microcapsule comprising a shell and a core, wherein the shell comprises a polymerized acrylate amine; wherein the composition has less than 100 ppm, less than 90 ppm, less than 80 ppm, less than 70 ppm, less than 60 ppm, less than 50 ppm, less than 40 ppm, less than 30 ppm, less than 20 ppm, less than 10 ppm, less than 5 ppm, or zero ppm, of a metal ion.

C. An anhydrous antiperspirant composition, comprising: a) an antiperspirant active; b) a perfume; and c) a microcapsule comprising a shell and a core, wherein the shell comprises a polymerized acrylate amine; wherein the microcapsule has less than 100 ppm, less than 90 ppm, less than 80 ppm, less than 70 ppm, less than 60 ppm, less than 50 pm, less than 40 ppm, less than 30 ppm, less than 20 ppm, less than 10 ppm, less than 5 ppm, or zero ppm, of a residual metal catalyst.

D. An anhydrous antiperspirant composition, comprising: a) an antiperspirant active; b) a perfume; and c) a microcapsule comprising a shell and a core, wherein the shell comprises a polymerized acrylate amine; wherein the microcapsule has less than 100 ppm, less than 90 ppm, less than 80 ppm, less than 70 ppm, less than 60 ppm, less than 50 pm, less than 40 ppm, less than 30 ppm, less than 20 ppm, less than 10 ppm, less than 5 ppm, or zero ppm, of a metal ion.

E. The antiperspirant composition of paragraphs A-D, wherein the antiperspirant active comprises aluminum zirconium tetrachlorohydrex gly; aluminum zirconium tetrachlorohydrate, aluminum zirconium pentachlorohydrate, aluminum zirconium pentachlorohydrex gly, aluminum zirconium trichlorohydrex gly, aluminum zirconium trichlorohydrate, aluminum zirconium octachlorohydrate, aluminum zirconium octachlorohydrex glycine, aluminum chlorohydrate, aluminum chlorohydrex polyethylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol or a combination thereof.

F. The antiperspirant composition of paragraphs A-E, wherein the perfume at least partially resides within the core.

G. The antiperspirant composition of paragraphs A-F, wherein the composition further comprises a structurant with a melt temperature of less than 85° C.

H. The antiperspirant composition of paragraph G, wherein the structurant comprises stearyl alcohol, hydrogenated castor wax, ozokerite, behenyl alcohol, polyethylene, polymethylene, a triglyceride, or a combination thereof.

I. The antiperspirant composition of paragraphs A-H, wherein the composition further comprises a liquid carrier.

J. The antiperspirant composition of paragraph I, wherein liquid carrier comprises a volatile fluid, a non-volatile fluid, a non-volatile silicone fluid, or a combination thereof.

K. The antiperspirant composition of paragraph J, wherein the volatile fluid comprises a volatile cyclic silicone fluid having from 3 to 7 silicone atoms.

L. The antiperspirant composition of paragraphs J-K, wherein the non-volatile fluid comprises mineral oil, PPG-14 butyl ether, isopropyl myristate, petrolatum, butyl stearate, cetyl octanoate, butyl myristate, myristyl myristate, $C_{12-15}$ alkylbenzoate, dipropylene glycol dibenzoate, PPG-15 stearyl ether benzoate, neopentyl glycol diheptanoate, octyldodecanol, isostearyl isostearate, octododecyl benzoate, isostearyl lactate, isostearyl palmitate, isononyl/isononoate, isoeicosane, octyldodecyl neopentanate, hydrogenated polyisobutane, isobutyl stearate, or combination thereof.

M. The antiperspirant composition of paragraphs J-K, wherein the non-volatile fluid comprises PPG 14 butyl ether, mineral oil, petrolatum, or a combination thereof.

N. The antiperspirant composition of paragraphs J-M, wherein the non-volatile silicone fluid comprises dimethicones, dimethicone copolyols, phenyl trimethicones, alkyl dimethicones, alkyl methicones, or a combination thereof.

O. The antiperspirant composition of paragraphs A-N, wherein the core comprises an oil mono, di- and tri-esters of $C_4$-$C_{24}$ fatty acids and glycerin; butyl oleate; hydrogenated castor oil; castor oil; mineral oil; capryllic triglyceride; vegetable oil; geranyl palmitate; silicone oil; isopropyl myristate; soybean oil; hexadecanoic acid; methyl ester; isododecane; or a combination thereof.

P. The antiperspirant composition of any of paragraphs A-O, wherein the polymerized acrylate amine shell comprises a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator.

Q. The antiperspirant composition of paragraphs A-P, wherein the polymerized acrylate amine comprises an aminoalkyl acrylate, alkyl aminoalkyl acrylate, dialkyl aminoalkyl acrylate, aminoalkyl methacrylate, alkylamino aminoalkyl methacrylate, dialkyl aminoalkyl methacrylate, tertiarybutyl aminoethyl methacrylate, diethylaminoethyl methacrylate, dimethylaminoethyl methacrylate, dipropylaminoethyl methacrylate, or a combination thereof.

R. The antiperspirant composition of paragraphs A-Q, wherein said polymerized acrylate amine is a diethylaminoethyl methacrylate, dimethylaminoethyl methacrylate, tertiarybutyl aminoethyl methacrylate, or a combination thereof.

S. The antiperspirant composition of paragraphs A-R, wherein the anhydrous antiperspirant composition is selected from the group consisting of a, a soft-solid antiperspirant, an invisible solid antiperspirant, an aerosol antiperspirant, and a fluid antiperspirant.

T. The antiperspirant composition of paragraphs A-S, wherein the microcapsules are in the form of a powder with a water content of less than 15%, by weight of the powder.

U. The antiperspirant composition of paragraphs A-T, wherein the metal catalyst or metal ion comprises tin, antimony, iron, copper, nickel, or a combination thereof; or tin, antimony, or a combination thereof.

V. The antiperspirant composition of paragraphs A-U, wherein the polymerized acrylate amine comprises a tertiary amine.

Test Methods

Penetration Force Value

Antiperspirant soft solid compositions can be evaluated for product hardness (gram-force) and defined in terms of penetration force values. "Penetration force value" as used herein can represent a force required to move a standard 45° angle penetration cone through the composition for a distance of 10 mm at a rate of 2 mm/second. Values can be measured at 27° C. and 15% relative humidity using a TA-XT2 Texture Analyzer, available from Texture Technology Corporation, Scarsdale, N.Y., U.S.A. Higher values represent a harder product and lower values represent a softer product. The cone is available from Texture Technology Corp., as part number TA-15, and can have a total cone length of about 24.7 mm, an angled cone length of about 18.3 mm, and a maximum diameter of an angled surface of the cone of about 15.5 mm. The cone can have a smooth, stainless steel construction and weigh about 17.8 grams.

To operate the TA-XT2 Texture Analyzer, the cone, or probe, can first be attached to a probe carrier arm and cleaned with a low-lint wipe. Subsequently, a top stop and a bottom stop can be checked to ensure each is in a desired position. Test samples will generally be the composition inside the consumer applicator. Once samples have been properly prepared by removing any top portion of the container so that the cone or probe has access to the composition in the package, a product sample can be placed on a test base. A template can be used to ensure the product sample is at a desired location on the test base such that the cone can be in a position to contact the product sample at a midpoint between a canister side and a canister screw.

After the cone can be adjusted to about 1 cm above the product sample, a "RUN" button on the Texture Analyzer can be pressed. A measurement can be taken by the Texture Analyzer while a canister containing the product sample is held. The cone can take a measurement and automatically disengage from the product sample. Two measurements can be taken for each canister.

Residual Catalyst/Ion Method for PMC Raw Material

Accurately weigh approximately 0.3 grams of an aqueous perfume microcapsule slurry raw material into a small volume microwave digestion vessel. Add 10 micrograms of Yttrium as an internal standard and dry the slurry in an oven at 105° C. for 30 minutes to remove excess water. Add 2 mL of concentrated nitric acid to the resulting solid and sonicate for 30 to 60 seconds to disperse. Digest in a sealed microwave digestion vessel (example: Milestone Ethos EZ) ramping to a temperature of 190° C. and holding for at least 5 minutes, but no more than 20 minutes, to complete digestion. Cool the vessel to ambient temperature, remove the digest, and dilute to 10 mL final volume for analysis.

Analyze the 10 mL solution by inductively coupled plasma atomic emission spectroscopy (example: Perkin Elmer Model 5300DV Inductively Coupled Plasma) using an internal standard approach and calibration standards that span the range from at least 0.1 micrograms per mL to 3 micrograms per mL (or wider, as appropriate.) Calculate the concentration in the original sample based on the measured concentration in the 10 mL digest and the original sample weight.

The yttrium emission at 371.029 nm was used as the internal standard reference. For antimony the emission wavelength 206.836 nm is used. For tin the wavelength 235.485 nm is used.

For a nominal 0.3 g sample, digested and diluted to 10 mL the calibration range would correspond to:

For low standard @ 0.1 micrograms per mL $$0.1 \text{ micrograms per mL} \times \frac{10 \text{ mL}}{0.3 \text{ gram}} =$$

3.3 micrograms per gram original sample

For high standard @ 3 micrograms per mL $$3 \text{ micrograms per mL} \times \frac{10 \text{ mL}}{0.3 \text{ gram}} =$$

100 micrograms per gram original sample

Residual Catalyst/Ion Method for Antiperspirant Composition

To measure for residual metal catalyst or metal ions in an antiperspirant composition utilize the analytical testing method in U.S. Pharmacopeia Chapter 233, Elemental Impurities—Procedures, copyright 2015 (official from May 1, 2016). For all samples, utilize a closed vessel digestion as the sample preparation method. When detecting iron, utilize Procedure 1 for (ICP-OES). When detecting other elements, utilize Procedure 2 (ICP-MS).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An anhydrous antiperspirant composition, comprising:
   a) an antiperspirant active;
   b) a perfume; and
   c) a microcapsule comprising a shell and a core, wherein the shell comprises a polymerized acrylate amine;
   wherein the composition has less than about 100 ppm of a metal ion; and
   wherein the microcapsule is friable and has a median volume weighted fracture strength from 0.5 to 25.0 mega Pascals (MPa); and
   wherein the shell has a thickness from 1 nanometer to 2000 nanometers.

2. The anhydrous antiperspirant composition of claim 1, wherein the metal ion comprises tin, antimony, iron, copper, nickel, or a combination thereof.

3. The anhydrous antiperspirant composition of claim 2, wherein the composition has less than 50 ppm of tin and/or antimony.

4. The anhydrous antiperspirant composition of claim 3, wherein the antiperspirant active comprises aluminum zirconium tetrachlorohydrex gly; aluminum zirconium tetrachlorohydrate, aluminum zirconium pentachlorohydrate, aluminum zirconium pentachlorohydrex gly, aluminum zirconium trichlorohydrex gly, aluminum zirconium trichlorohydrate, aluminum zirconium octachlorohydrate, aluminum zirconium octachlorohydrex glycine, aluminum chlorohydrate, aluminum chlorohydrex polyethylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol or a combination thereof.

5. The anhydrous antiperspirant composition of claim 3, wherein the perfume at least partially resides within the core.

6. The anhydrous antiperspirant composition of claim 3, wherein the composition further comprises a structurant with a melt temperature of less than 85° C.

7. The anhydrous antiperspirant composition of claim 6, wherein the structurant comprises stearyl alcohol, hydrogenated castor wax, ozokerite, behenyl alcohol, polyethylene, polymethylene, a triglyceride, or a combination thereof.

8. The anhydrous antiperspirant composition of claim 3, wherein the polymerized acrylate amine shell comprises a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator.

9. The anhydrous antiperspirant composition of claim 3, wherein said polymerized acrylate amine is a diethylaminoethyl methacrylate, dimethylaminoethyl methacrylate, tertiarybutyl aminoethyl methacrylate, or a combination thereof.

10. The anhydrous antiperspirant composition of claim 3, wherein the microcapsules are in the form of a powder with a water content of less than 15%, by weight of the powder.

11. An anhydrous antiperspirant composition, comprising:
    a) an antiperspirant active;
    b) a perfume; and
    c) a microcapsule comprising a shell and a core, wherein the shell comprises a polymerized acrylate amine;
        wherein the composition has less than about 100 ppm of a residual metal catalyst; and
        wherein the microcapsule is friable and has a median volume weighted fracture strength from 0.5 to 25.0 mega Pascals (MPa); and
        wherein the shell has a thickness from 1 nanometer to 2000 nanometers.

12. The anhydrous antiperspirant of claim 11, wherein the residual metal catalyst comprises tin, antimony, iron, copper, nickel, or a combination thereof.

13. The anhydrous antiperspirant of claim 12, wherein the perfume at least partially resides in the core.

14. The anhydrous antiperspirant composition of claim 13, wherein the microcapsules are in the form of a powder with a water content of less than 15%, by weight of the powder.

15. The anhydrous antiperspirant composition of claim 14, wherein the polymerized acrylate amine shell comprises a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator.

16. The anhydrous antiperspirant composition of claim 14, wherein said polymerized acrylate amine is a diethylaminoethyl methacrylate, dimethylaminoethyl methacrylate, tertiarybutyl aminoethyl methacrylate, or a combination thereof.

17. An anhydrous antiperspirant composition, comprising:
    a) an antiperspirant active; and
    b) a microcapsule comprising a shell and a core, wherein the shell comprises a polymerized acrylate amine and the core comprises a perfume;
        wherein the microcapsule has less than 100 ppm of a residual metal catalyst;
        and
        wherein the microcapsule is friable and has a median volume weighted fracture strength from 0.5 to 25.0 mega Pascals (MPa); and
        wherein the shell has a thickness from 1 nanometer to 2000 nanometers.

18. The anhydrous antiperspirant composition of claim 17, wherein the residual metal catalyst comprises tin, antimony, iron, copper, nickel, or a combination thereof.

19. The anhydrous antiperspirant composition of claim 18, wherein said polymerized acrylate amine is a diethylaminoethyl methacrylate, dimethylaminoethyl methacrylate, tertiarybutyl aminoethyl methacrylate, or a combination thereof.

20. The anhydrous antiperspirant composition of claim 19, wherein the microcapsule has less than 30 ppm of the residual metal catalyst selected from the group consisting of tin, antimony, and a combination thereof.

* * * * *